United States Patent [19]

Schmidt

[11] Patent Number: 5,916,553
[45] Date of Patent: *Jun. 29, 1999

[54] COMPLEX FOR INDUCING BONE GROWTH IN THE MASTOID CAVITY

[76] Inventor: Karlheinz Schmidt, Aeussere Weilest. 12, Gomaringen 72810, Germany

[*] Notice: This patent is subject to a terminal disclaimer.

[21] Appl. No.: 08/474,150

[22] Filed: Jun. 7, 1995

Related U.S. Application Data

[63] Continuation-in-part of application No. 08/350,666, Dec. 7, 1994, which is a continuation of application No. 07/849,083, Sep. 17, 1992, abandoned, and a continuation-in-part of application No. 08/313,113, Dec. 7, 1994, abandoned.

[51] Int. Cl.[6] .................................................. A61K 45/05
[52] U.S. Cl. ......................... 424/85.1; 424/422; 514/12; 623/16
[58] Field of Search ............................. 514/12; 424/85.1, 424/422

[56] References Cited

U.S. PATENT DOCUMENTS

| | | |
|---|---|---|
| 4,294,753 | 10/1981 | Urist . |
| 4,404,134 | 9/1983 | Becker et al. . |
| 4,472,840 | 9/1984 | Jefferies . |
| 4,642,120 | 2/1987 | Nevo et al. . |
| 4,681,763 | 7/1987 | Nathanson et al. . |
| 4,693,718 | 9/1987 | Urry et al. . |
| 4,703,108 | 10/1987 | Silver et al. . |
| 4,732,155 | 3/1988 | Zetter et al. . |
| 4,832,686 | 5/1989 | Anderson . |
| 4,863,732 | 9/1989 | Nathanson et al. . |
| 4,925,124 | 5/1990 | Silver et al. . |
| 4,932,973 | 6/1990 | Gendler ..................................... 623/16 |
| 4,950,483 | 8/1990 | Ksandor et al. ........................ 424/422 |
| 4,973,466 | 11/1990 | Reich . |
| 5,019,087 | 5/1991 | Nichols . |
| 5,024,841 | 6/1991 | Chu et al. ............................... 424/422 |
| 5,041,138 | 8/1991 | Vacanti et al. . |
| 5,556,430 | 9/1996 | Gendler ..................................... 623/16 |

FOREIGN PATENT DOCUMENTS

| | | |
|---|---|---|
| 271668A1 | 6/1988 | European Pat. Off. . |
| 2637502A1 | 4/1990 | France . |
| 2137209 | 10/1984 | United Kingdom . |
| 2215209 | 9/1989 | United Kingdom . |
| 84/00540 | 2/1984 | WIPO . |
| 00540 | 8/1984 | WIPO . |
| 88/07078 | 9/1988 | WIPO . |
| 90/00060 | 1/1990 | WIPO . |

OTHER PUBLICATIONS

International Search Report (English).
Furcht et al., Lab Investigation, vol. 55(5), 505–509(1916) Editorial Critical Factors . . .
Dijke et al, "Growth Factors for . . . Healing", Biotechnology, vol. 7, pp. 793–798(1959).

Primary Examiner—Cecilia Tsang
Assistant Examiner—Patrick R. Delaney
Attorney, Agent, or Firm—Blank Rome Comisky & McCauley LLP

[57] ABSTRACT

A protein complex for inducing growth of bone in the maxillary sinus of an animal is disclosed. The complex is generally made from animal bone, defated, demineralized, ground, slurried, and fractionated ssuch that functional structural, adhesive, chemotaxis, and growth components are isolated and purified.

13 Claims, 5 Drawing Sheets

COMPLEX FOR INDUCING BONE GROWTH IN THE MASTOID CAVITY

CROSS-REFERENCE TO RELATED APPLICATION

This is a continuation-in-part of pending application Ser. No. 08/350,666, filed Dec. 7, 1994, now pending, which, in turn, is a continuation of application Ser. No. 07/849,083, filed Sep. 17, 1992, now abandoned. This is also a continuation-in-part of application Ser. No. 08/313,113, filed Dec. 7, 1994 now abandoned. The subject matter of each of the aforementioned applications is incorporated herein by reference.

FIELD OF THE INVENTION

The present invention relates generally to a complex or material capable of stimulating new bone growth and, more particularly, to the use of this complex to reossify mastoid cavities such as the cavity created following the surgical removal of a cholesteatoma.

BACKGROUND OF THE INVENTION

Various techniques and materials exist for stimulating bone growth, necessitated by trauma, disease, or surgery. Examples of such materials and techniques may be found in Bourne, *Biochemistry and Physiology of Bone* (Academic Press).

An example of a surgical procedure which creates a need for post operative bone regrowth is cholesteatoma treatment. A cholesteatoma is a cyst or cystlike tumor affecting the middle ear or the bone of the mastoid. The condition leads to erosion of bone, including the ear ossicles (the tiny bones of the middle ear). Surgical treatment of cholesteatoma is problematic as it leaves an open hole in the auditory canal due to the removal of the rear auditory canal wall. This causes problems with the postoperative care of the mastoid cavity. The epithelium which coats the mastoid cavity lacks the capability to export cutaneous scales and earwax as does the auditory canal epithelium. This leads to a collection in the cavity which can result in damage to the coating with the creation of granulations and secretions. Between 10 and 40% of the patients with mastoid cavities suffer from continual or repetitively recurrent secretions after the operation. The shape and size of the cavity can adversely affect the hearing. The vestibule is more easily irritated by thermal stimuli, so that the patient with an open mastoid cavity must close the ear when swimming.

Following surgery there is the danger of the recurrence of a cholesteatoma either through unremoved squamous epithelium cells or through a renewed collection of auditory canal skin. To permanently correct the problem an osteoinductive substance should be employed to which the adjacent tissue could be stimulated for the purpose of reossification.

Attempts to avoid or to minimize the surgical cavity causes increased risk of cholesteatoma recurrence or a large surgical expenditure. A lasting obliteration of the surgical cavity with a suitable material could utilize the advantages of the radical operation and avoid its disadvantages at the same time. Accordingly, reconstruction or regrowth of the auditory bones would be most desirable.

SUMMARY OF THE INVENTION

The ability to regrow bone in a cavity of any significant size has heretofore been largely unknown. The material of the present invention fills this void literally and figuratively. This invention is directed to solving this heretofore unanswered problem by providing a complex or material useful in inducing bone regrowth in cavities created in bone tissue by surgery, disease or injury so as to regrow bone and fill the cavity. This invention relates to a method for effectively utilizing this complex by inducing mastoid bone growth in cholesteatoma patients.

The complex accordingly can be isolated from almost any mammalian bone, although calf bone is preferred due to its availability in sufficient quantities. In short, the material is isolated by a procedure comprising the steps of: removing the ends of the bone, splitting the bone, removing the marrow, defatting the bone, dissolving the mineral part of the bone in acid, fractionating the remaining proteins by a process of fractional precipitation of the proteins followed by dialysis and lyophilization. According to this method a protein complex is recovered. The protein complex comprises a chemotaxic component which attract bone stem cells from healthy tissue, structural and adhesive components and provides a framework to which the attracted stem cell may bind, be supported and grow. In addition, the recovered protein complex includes maturation components which enables the stem cells to divide and mature into osteocytes.

The protein complex of the present invention has a semi-plastic consistency allowing it to be packed into a cavity in the bone. Once the cavity is packed, the complex will recruit bone stem cells, provide a framework for the stem cells to adhere, and stimulate growth and maturation of bone cells, which, in turn, make bone proteins.

The complex according to the present invention has been successfully employed in both animal and human trials, the results of which are set forth hereinafter. The following abbreviations will be sometimes used for convenience:

HA=Hydroxyapatite Ceramic;
BIC=Complex or Bone Inducing Complex;
HE=Hematoxylin-Eosin-Dye.

With the foregoing and other objects, advantages and features of the invention that will become hereinafter apparent, the nature of the invention may be more clearly understood by reference to the following detailed description of the invention, the appended claims and to the several view illustrated in the attached drawings.

DETAILED DESCRIPTION OF THE INVENTION

Figure 1:
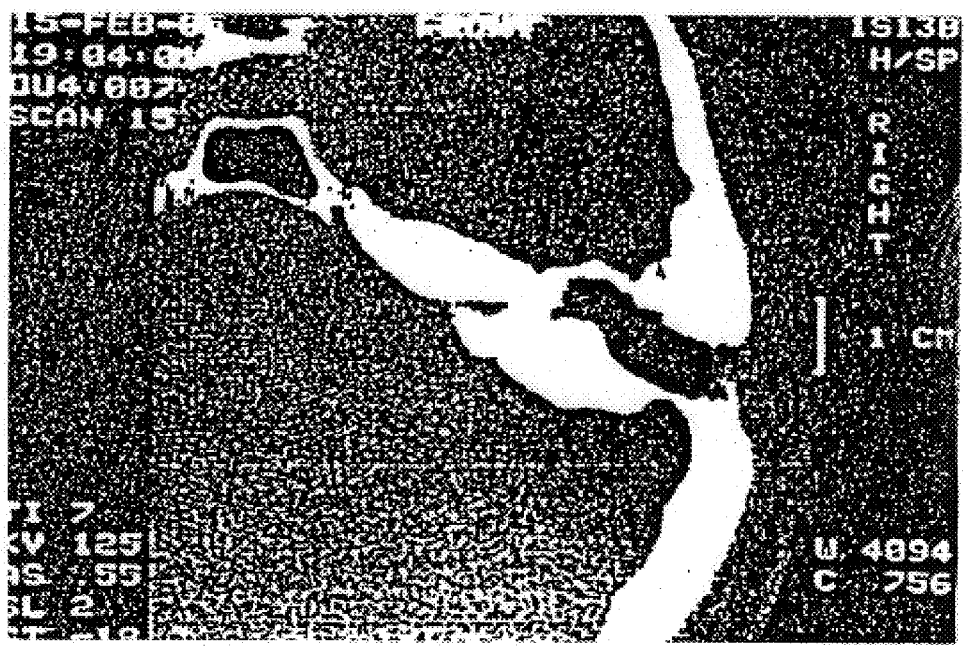
FIG. 1 is a computer tomogram of the petrosal bone 2 months after the implantation of the complex. The inserted substance lies on the floor of the enlarged auditory canal. Reossification beginning on the edges at the contact point can be recognized.

The complex of the present invention is isolated according to the method described in my copending U.S. patent applications Ser. Nos. 08/313,113 and 07/849,083, both of which are incorporated herein by reference in their entireties. Also, a method of producing the BIC of the present invention, and an in vitro analysis thereof, is described in Joos et al., "Effects of a New Bone-Inducing Biomaterial on Mesenchymal Cells in Vitro", *Artificial Organs,* 16(4), pgs. 354—360, 1992.

The complex can be isolated from almost any mammalian bone, although calf bone is preferred due to its availability in large quantities. Briefly, the complex is isolated by the steps: removing the ends of the bone, splitting the bone, removing the marrow, defatting the bone, dissolving the mineral part of the bone in acid, fractionating the remaining proteins by fractional precipitation of the proteins followed by dialysis. A protein complex is recovered comprising a chemotaxic component to attract bone stem cells from healthy tissue, structural and adhesive components to provide a framework to which the attracted stem cell may bind and be supported and growth and maturation components so that the stem cells will divide and mature into an osteocytes.

The presently preferred method by which complex according to the present invention may be isolated is illustrated by the following non-limitative example.

EXAMPLE I

Isolation of the bone regrowth complex

Sterile tubular bones from 3 month old calves of both genders were freed from any attached soft tissues. The condyles were sawed off and the diaphysial sections of the bones were split lengthwise. The bone marrow was removed by high pressure washing (200 bar) with water. The bone pieces were defatted in a six fold amount (weight per volume) of a 1 to 1 mixture of chloroform and methanol. The bone pieces were then deep frozen in liquid nitrogen. The deep frozen bone is ground in a liquid nitrogen cooled, sterile, ball mill to an average particle size of 700 micrometers. The ground bone is slurried with a 10 fold excess (weight per volume) of 0.5 N hydrochloric acid at room temperature for 24 hours. The solution is centrifuged at 5000×60 minutes. The precipitate is isolated and washed with sterile water until all the acid is removed. The neutralized precipitate is dried in a sterile stream of nitrogen until the water content is about 30%. The dried precipitate is then added to an aqueous solution of a chaotropic compound (for example 4 M guanidinium thiocyanate or 8 M urea) for 12 hours at room temperature to denature the proteins. The solution is centrifuged at 5000 g for 60 minutes and the solution containing the soluble, denatured proteins is retained. The bone growth material of the present invention is isolated from the soluble portion by fractionating by means of ultrafiltration.

Ultrafiltration is performed in a conventional flat bed or hollow-fiber system with a cut-off of the filter of 3000 Dalton. Subsequently, the active protein complex containing the essential functional components is obtained by fractionated precipitation and centrifugation at 5000 g for 60 minutes, resuspended in water and lyophilized.

The identification of the components of the complex according the present invention does not yield a specific compounds, as for example a single adhesion or recruiting component. For example, the adhesion components are isolated in the form of a complete fraction which includes not one compound with adhesive characteristics, but rather several or even numerous compounds, that have adhesive characteristics.

The protein complex or BIC recovered according to the method of the present invention comprises components, each of which may be tested for by the techniques described below:

Structural component:

The structural component comprising primarily collagens and proteoglycans functions as the framework of the complex to contain the other components. This component is identified through cell homing. After implantation into a recipient organism the complex provides a homing structure for mesenchymal cells, a process which can be followed by morphological examination.

Recruiting component:

The recruiting component which attract, bone stem cells, is identified by the following procedure.

In a Boyden chamber (described in S. Boyden, *J. Exp. Med.,* v. 115, pp.435+, 1962) the individual fractions separated by ultrafiltration are tested for chemotactic activity by using two plexiglass chambers which are divided by a penetrable porous membrane for connective tissue cells. In the one chamber one puts in mesenchymal cells, while the fraction to be studied for cell recruiting is situated in the other chamber divided by the membrane. The recruiting activity of the fraction occurs as a function of the number of cells active through the membrane pores in a unit of time. In this way the appropriate fraction is ascertained.

Adhesive component:

The adhesive component which functions to adhere the stem cells to the structural component is determined immunologically by interaction of the fraction to be tested with anti-adhesive antibodies against the adhesive proteins through radial immunodiffusion, by immunoelectrophoresis of the Rocket technique or by means of nephelometry in microfilter plates.

Cell adhesion to a surface is quantified by rinsing a cell layer on the surface with a fluid with increasing shear forces and counting the adhering cells after this procedure. Alternatively, adhesion proteins can be identified by use of specific antibodies which are commercially available by conventional immunodiffusion, immunoelectrophoresis or nephelometry.

Growth and/or Maturation Components:

The growth/maturation component which produces cell differentiation is identified from the fractions, wherein cultivated mesenchymal cells are exposed to the fraction to be tested and the expression of bone specific marker molecules, as for example alkaline phosphatase or osteocalcin, are measured.

One bone-specific marker molecule is osteocalcin which is measured by a specific enzyme-linked immuno assay (ELISA). Also bone-specific alkaline phosphatase can be used as a marker. The activity of this enzyme is measured by colorimetry using p-nitrophenyl-phosphate as a substrate.

The fractions determined in this way, which comprise the components of the complex according to the present invention, are unified, dialyzed fully against sterile distilled water and subsequently subjected to a sterile lyophilization.

Figure 2:
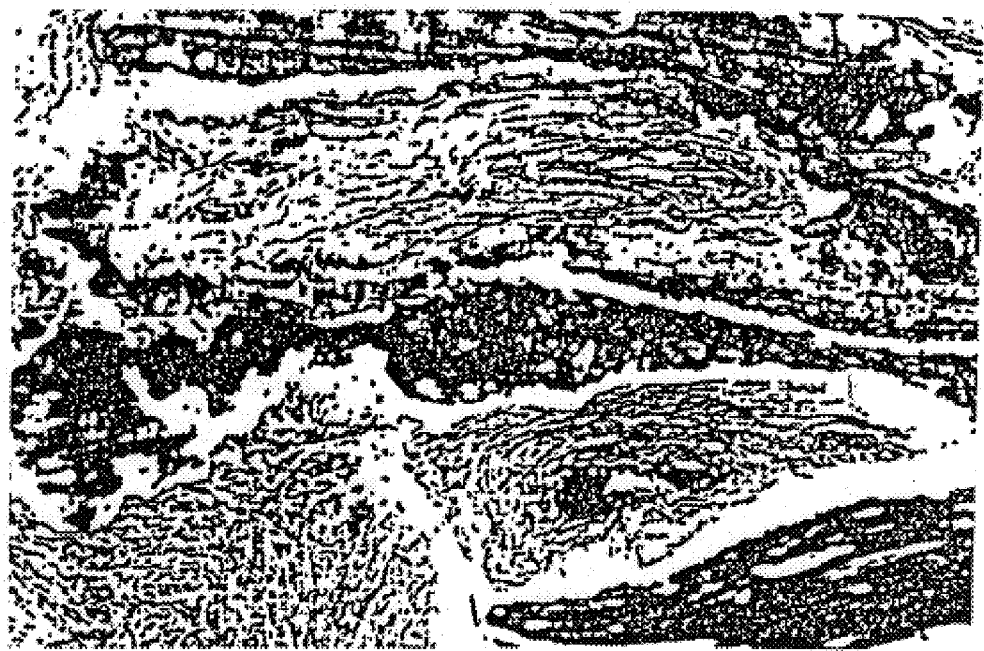
FIG. 2 is a photograph showing the bone growth complex 4 months after the implantation in the mastoid cavity of a patient. A partial reossification within the implanted substance can be recognized (HE, 40x).
Figure 3:
FIG. 3 is a photograph of cut through the middle ear of the rabbit with auditory canal, ear drum, recessus epitympanicus (HE 6x).
Figure 4:
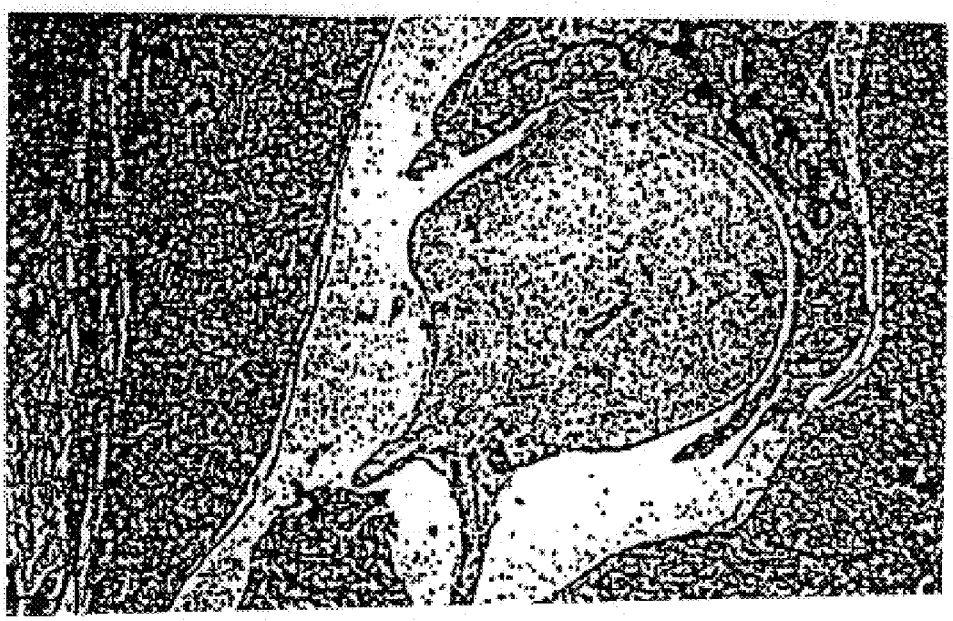
FIG. 4 is a photograph showing cut through the recessus epitympanicus with anvil, as well as a shell-like reossification 4 weeks after the implantation of the complex of the present invention (HE 25x).
Figure 5:
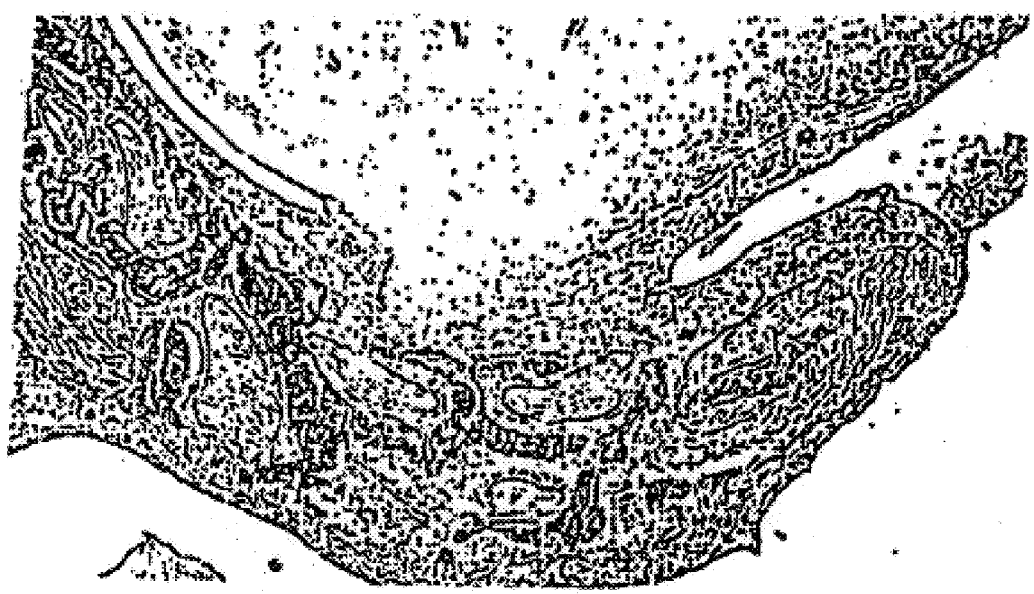
FIG. 5 is a photograph showing reossification in direct connection with the anvil 4 weeks after the implantation of BIC (HE 63x).
Figure 6:
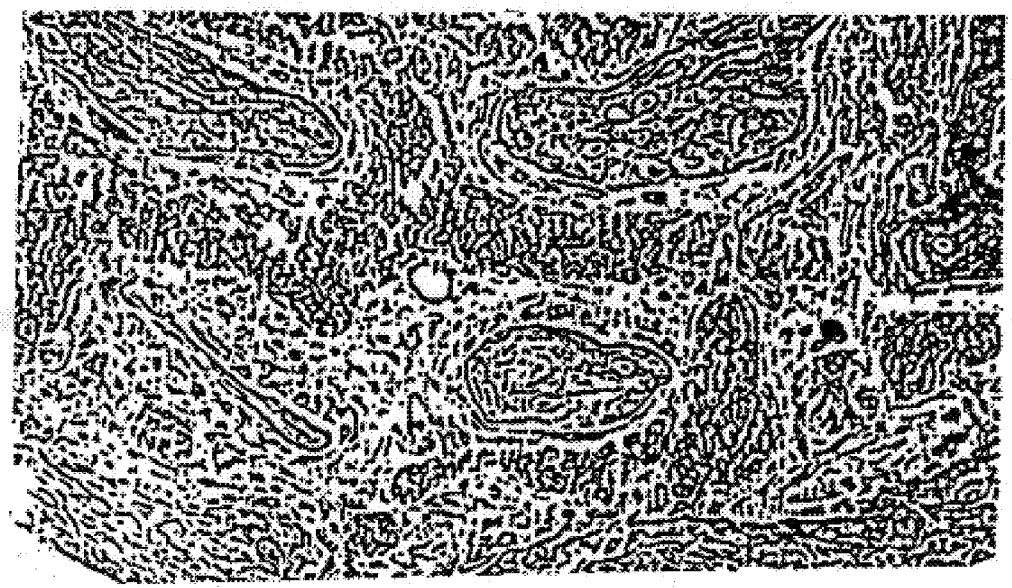
FIG. 6 is a photograph showing bone formation in the recessus epitympanicus, surrounded by numerous capillaries and vessels, 4 weeks after the implantation of BIC (HE 160x).
Figure 7:
FIG. 7 is a photograph of the recussus epitympanicus; rest of ceramic with grown-in bone tissue; 4 weeks after implantation of HA+BIC (HE 25×).

The lyophilisate contained in this form can be inserted directly for producing the biological part (in this case bone), but can also be diluted or joined with another material depending on the size, etc. of the cavity to be filled. For example the complex may (a) coat an orthopaedic or dental implants (metal, ceramic or others) as shown in FIG. 2, (b) fill titanium or polymer containers, wire mesh, or baskets in order to augment bone mass as shown in FIG. 3, or (c) combine with biocompatible resorbable synthetic polymers or biopolymers (native or chemically modified collagens, polylactides, polyglycolides or copolymers with other synthetic polymers) as solid or porous material, as a gel or foam or as an injectable suspension or solution. This also constitutes a slow release system for the protein complex. The complex can be coupled to solid surfaces by dipping the materials into a solution and subsequent lyophilization.

A characteristic of the complex of the present invention is that solutions of the components in proportions as they are obtained from the same amount of starting material are mixed under high ionic strength and the complex is formed by desalting according to well known conventional techniques such as dialysis. The complex is a new entity which is not present in this form in the starting material it is formed and stabilized by protein-protein interactions.

The complex can be obtained sterile by filtration of the components before complex formation or by subsequent sterilization procedures such as gamma-irradiation.

A variation on the above-described isolation method which may be employed, is disclosed in my co-pending application Ser. No. 08/313,113, incorporated herein by reference.

EXAMPLE II

Use of complex for cholesteatoma (human)

An example of a preferred method by which the complex made in EXAMPLE I may be used clinically is illustrated in the following non-limitative Example.

Surgery was performed on 11 patients (7 men 4 women ranging in age from 11 to 57 years) who had been previously operated on for a cholesteatoma but had to be operated on again due to a recurrence of the cholesteatoma. In all patients the mastoid process had an unfavorable shape from the prior operation. Deep sinuses were found consistently in the bone, in which earwax and shed epithelium cells congested thereby resulting in recurrence of the cholesteatoma.

The complex of the present invention was prepared in 1–2 g portions and sterilized under pressure with ethylene oxide (gas sterilization).

In all of the patients the mastoid cavity was enlarged and the recurrence of cholesteatoma removed by milling out the mastoid. The deep cell features and sinuses resulting from this were filled an appropriate amount of complex which was determined by filling the cavity with water or saline solution and measuring the volume thereof. The implanted substance and the largest part of the cavity were covered with mesenchymal tissue and the ear packed in the customary fashion.

After the operation the patients were observed for another week. Three weeks after the operation the packing was removed and after another week the patients appeared for a follow-up examination. During these four weeks the patients received no additional medication.

The operation of the patients and the implantation of the material went without problems. In all of the patients, the area operated on healed and without inflammation. No foreign body reaction was observed. A computer tomogram of a patient 2 months after the implantation shows a reossification beginning on the edges on the contact point of the implanted material (FIG. 1).

For the follow-up operation of a patient for hearing improvement 4 months after the implantation of material, tissue was taken from the mastoid cavity coating, that was macroscopically healed without irritation. The histological examination shows a reossification within the implanted material (FIG. 2). No foreign body reaction occurred.

In all of the patients, the implanted bone regrowth material healed without irritation. The mastoid cavities had the desired shape and were coated in nonirritated squamous epithelium. They could be shaped clearly and in a reduced fashion. The patients had no problems with their mastoid cavities four weeks after the operation. Furthermore, the post-operative care was made easier.

The shape of the newly formed bone is determined by the geometry in which the complex is implanted, physiological remodelling of the new bone causes the final function adaptation to the biomechanical requirements.

Despite differences in bone architecture, bone induction by the complex works successfully as long as inducible living cells are available for recruiting, homing, adhesion and differentiation.

Experiments set forth herein and in my copending applications evidence this.

EXAMPLE III

Use of complex in animal trials

An osteo-inductive bone protein inducing complex in substantially pure form was implanted in the recessus epitympanicus of rabbit ears in combination with support materials hydroxyapatite and a collagenic fleece. The suitable support materials offers the advantage that small amounts of the complex are not washed away by cleaning or the blood stream.

The osseous structure of the mastoid cavity was studied in this work after the implantation of a bone inducing protein complex. Therefore the bone inducing complex, alone or coupled to the support material hydroxyapatite or collagen, was implanted in the recessus epitympanicus of rabbit ears. After 4 and 8 weeks, respectively, complex induced a reossification, clear from the morphology, both alone and when coupled to the support material implantations. In the case of the coupled complex the support material was used as a "guide rail" for the osseous structure. Reossification increased after the 8 week period.

Materials and Methods

Materials

Year-old domestic rabbits (male and female) with a weight of 3000–4000 g were used as test animals. The keeping was in a climate-controlled animal cage at 23° C. at 50% relative humidity. The support material HA (Osprovit R) was received from the company Feldmuhle AG, in Plochingen, as a sterile porous granulate with 0.8 mm sized grains; total pore volume: ca. 60%, macropore size: 100–400 $\mu$m, micropore size: <5 $\mu$m approximately 6–8% of the total pore number, content of hydroxyapatite: >90%, specific area 0.61 m$^2$/g, solubility in water: 0.6 mg Ca$^{2+}$/100 ml.

The collagen Lyostypt® was obtained from Braun AG, in Melsungen Germany. According company information to collagen is pure, native and resorbable beef collagen fibrils.

Isolation of the Complex:

The bone-inducing protein complex (BIC) was isolated from bone as a source material as described. The activity of the BIC is employed in the musculature of the stomach of a rat. 50 mg of the complex was implanted in a small pouch of the abdominal wall muscle of a rate and bone formation checked after 20 days by morphological examination.

Production of the Implant

To coat the support material with BIC, 1 ml of an aqueous BIC solution (3 mg/ml) was added to 100 mg HA and 50 mg collagenic fleece and immediately frozen in liquid nitrogen after thorough mixing to prevent separation of the component. After subsequent lyophilization, the lyophilisate was compressed and implanted.

The control implants were produced only with an analogous 1 ml double distilled water each. A 3 mg dosage of pure BIC was implanted directly after isolation and purification.

Insertion of the Implant

After anesthetizing the rabbits with an Evipan sodium solution (1:20 dilution) and additional local anesthetics on the cerumen insertion (xylocain 0.5% with suprarenin additive) the outer auditory canal and the middle ear were opened by creating a meatotympanal flap which encloses the flaccid part. Through this operation the recessus epitympanicus was freely accessible and the implant of pure BIC, HA coated with BIC or collagen plus BIC—was inserted. Afterwards, the tympanomeatal flaps were moved back so that the middle ear closed. The opening in the chondral section of the auditory canal was sutured and the rest of the wound was provided with a subcutaneous suture and skin sutures. The support material coated with BIC was inserted in the recessus epitympanicus of the right ear in each case, while the corresponding control preparation was inserted in the left ear. Pure BIC was inserted in the recessus epitympanicus of either the right or left ear.

Explantation and Regeneration of the Explants

Four and eight weeks, respectively, after the operation the rabbits were killed and the ears explanted with the entire petrosal bone. After the removal of the muscle attachments, tendons and skin, the preparation is set for two days in 6% buffered formalin solution and subsequently laid in a 37° C. warm EDTA solution for 12 weeks for decalcification, whereby the solution is changed weekly. After the decalcification, the preparations were trimmed for embedding and dehydrated in a rising alcohol row and xylol. With the dehydration, a hardening is achieved through the increase in the consistency of the tissue for one, and for another makes embedding in paraplast possible.

Fifteen cuts are produces from each preparation and dyed with hematoxylineosin (HE) as follows: for reconduction into a water-soluble state with rotihistol, rising alcohol row and double distilled water, 15 minute dyeing with hemalum, tint blue for 10 minutes in tap water, dye with eosin 45 seconds, dehydrate with rising alcohol row to rotihistol, cover up in eukitt.

Through this dyeing process the cell nuclei are dyed blue and the cytoplasm, collagen fibers and erythrocytes are dyed red.

Results

In the histological cuts that were produced from the recessus epitympanicus, a vascular tissue, which lies like a shell around the anvil and is connected directly with it, was produced 4 weeks after the implantation of pure BIC. Collections of erythrocytes are in this tissue and numerous morphological detectable bone fragments are enclosed, the osteoblasts and osteocytes are included (Table 1, FIGS. 3–6).

TABLE 1

Implantation of pure BIC in the recessus epitympanicus; K803 and K804 in the right recessus, K801, K802, K805, K806 in the left recessus; a reossification occurred in 5 of 6 rabbits.

| Animal No. | Length of time | Right recessus | Re-ossification | Left recessus | Re-ossification |
|---|---|---|---|---|---|
| K801 | 4 weeks | collagen + BIC | + | pure BIC | + |
| K802 | 4 weeks | collegan + BIC | + | pure BIC | + |
| K803 | 4 weeks | pure BIC | + | — | – |
| K804 | 4 weeks | pure BIC | + | — | – |
| K805 | 4 weeks | collagen + BIC | + | pure BIC | + |
| K806 | 4 weeks | collagen + BIC | + | pure BIC | – |

In the rabbits which were implanted with BIC coated HA, after 4 weeks the coated support material in the right recessus was surrounded by newly formed bone tissue and vessels in 6 of 8 animals. Collections of erythrocytes were grouped partially around this. The porous arrangement of the HA made a growth of the bone on the support material possible as well, so that thick fragments of bone can be detected in the deep. The rest of the support materials were still recognizable in this stage (Table 2, FIGS. 5 and 6).

The uncoated HA implanted in the left recessus epitympanicus of the control animals led to reossification in only 3 of the animals. This was significantly less however in comparison to the bone formation that was induced by the BIC coated HA (Table 2).

With the exception of fewer granulocytes and lymphocytes in the vicinity of the implant no foreign body or inflammation reaction occurred.

TABLE 2

Implant of BIC coated HA (right recessus) and uncoated HA (left recessus); reossification after 4 weeks

| Animal No. | Length of time | Right recessus | Re-ossification | Left recessus | Re-ossification |
|---|---|---|---|---|---|
| K818 | 4 weeks | HA + BIC | – | HA | – |
| K819 | 4 weeks | HA + BIC | – | HA | – |
| K820 | 4 weeks | HA + BIC | + | HA | – |
| K845 | 4 weeks | HA + BIC | + | HA | + |
| K846 | 4 weeks | HA + BIC | + | HA | + |
| K847 | 4 weeks | HA + BIC | + | HA | + |
| K850 | 4 weeks | HA + BIC | + | HA | – |
| K851 | 4 weeks | HA + BIC | + | HA | – |

Figure 9:
FIG. 9 is a photograph showing heavy reossification on the edge and on the inside of the support material with surrounding erythrocytic edge, 8 weeks after the implantation of HA+BIC (HE 63×).

Eight weeks after the implantation an advanced reossification appears in 4 of 5 test animals, originating in the mucus membrane covered wall of the auditory canal, into the coated support material, while bone formation was seen exclusively on the edge of the implant in only two of the control animals (Table 3, FIG. 9).

TABLE 3

Implantation of BIC coated HA (right recessus) and of uncoated HA (left recessus); reossification after 8 weeks

| Animal No. | Length of time | Right recessus | Re-ossification | Left recessus | Re-ossification |
|---|---|---|---|---|---|
| K810 | 8 weeks | HA + BIC | – | HA | + |
| K811 | 8 weeks | HA + BIC | + | HA | – |

TABLE 3-continued

Implantation of BIC coated HA (right recessus) and of uncoated HA (left recessus); reossification after 8 weeks

| Animal No. | Length of time | Right recessus | Re-ossification | Left recessus | Re-ossification |
|---|---|---|---|---|---|
| K812 | 8 weeks | HA + BIC | + | HA | − |
| K813 | 8 weeks | HA + BIC | + | HA | − |
| K814 | 8 weeks | HA + BIC | + | HA | + |

Figure 8:
FIG. 8 is a photograph of an edge from the grown-in tissue with strong capillarization and bone formation (HE 400×).

Four weeks after the implantation of BIC+collagen, the implant was almost completely replaced with fibrous tissue in 7 of 11 animals, in which cartilage or bone fragments were set in. The newly formed tissue had a broad base connection with the back wall of the recessus epitympanicus. Collections of erythrocytes and osteocytes or cartilage cells were enclosed in this tissue (Table 4, FIGS. 8 and 9).

TABLE 4

Implantation of collagen + BIC (right recessus) and pure collagen or pure BIC (left recessus); reossification after 4 weeks

| Animal No. | Length of time | Right recessus | Re-ossification | Left recessus | Reossification |
|---|---|---|---|---|---|
| K817 | 4 weeks | Collagen + BIC | + | Collagen | − |
| K842 | 4 weeks | Collagen + BIC | − | HA | − |
| K843 | 4 weeks | Collagen + BIC | − | HA | − |
| K844 | 4 weeks | Collagen + BIC | − | HA | − |
| K848 | 4 weeks | Collagen + BIC | − | HA | − |
| K849 | 4 weeks | Collagen + BIC | + | HA | − |
| K853 | 4 weeks | Collagen + BIC | + | HA | − |
| K801 | 4 weeks | Collagen + BIC | + | BIC | + |
| K802 | 4 weeks | Collagen + BIC | + | BIC | + |
| K805 | 4 weeks | Collagen + BIC | + | BIC | + |
| K806 | 4 weeks | Collagen + BIC | + | BIC | − |

The complex of the present invention can also be used in a large number of clinical indications such as traumatic defects in the bone (fractures), atrophy of bone mass, cysts, tumors, metastasis, inflammatory bone defects, defects by surgical intervention after extraction of teeth, periodontal disease, localize degenerative disorders in the bone, genetic disorders and malformation e.g. in maxillo-facial surgery. It may be used in bones of the skull as well as in long bones or bones of the spine. It may be indicated in both humans and animals (e.g. in race horses, dogs, etc.)

Although presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. A method of isolating a complex for stimulating bone growth comprising the steps of:

providing a bare diaphysial bone section;

grinding said bare bone into small particles;

slurrying said bone particles in an acid;

centrifuging said slurry to yield insoluble protein;

drying said protein;

denaturing said dried protein with a chaotropic compound; and isolating the complex from the denatured protein by fractional precipitation of the proteins;

wherein said isolated complex includes a bone derived chemotactic component to attract bone stem cells from healthy tissue, bone derived structural and bone derived adhesive components to provide a framework to which the attracted stem cells may bind and be supported and bone derived growth and maturation components so that the stem cells will divide and mature into osteocytes.

2. The method of claim 1 wherein said bone is animal bone.

3. The method of claim 1 wherein said bone is frozen prior to grinding.

4. The method of claim 1 wherein said bone pieces are defatted in an organic solvent.

5. The method of claim 4 wherein said solvent is a six fold amount (weight per volume) of a 1 to 1 mixture of chloroform and methanol.

6. The method of claim 3 wherein said bone is frozen in liquid nitrogen before grinding.

7. The method of claim 1 wherein ultrafiltration is performed in a flat bed or hollow-fiber system.

8. The method of claim 1 wherein said isolated complex comprises a bone derived chemotaxic component to attract bone stem cells from healthy tissue, bone derived structural and bone derived adhesive components to provide a framework to which the attracted stem cell may bind and be supported, and bone derived growth and maturation components so that the stem cells will divide and mature into osteocytes.

9. A complex for reossification in the mastoid cavity of a human made according to the method of claim 1.

10. Substantially isolated and purified bone growth complex comprising a bone derived chemotaxic component to attract bone stem cells from healthy tissue, bone derived structural and bone derived adhesive components to provide a framework to which the attracted stem cell may bind and be supported, and bone derived growth and maturation components so that the stem cells will divide and mature into osteocytes.

11. A method of stimulating the formation of new bone in a mastoid cavity of a patient following removal of a cholesteatoma comprising the steps of:

filling the mastoid cavity with the substantially isolated and purified bone growth complex of claim 10.

12. The method according to claim 11 comprising the additional steps of:

filling the mastoid cavity with the substantially isolated and purified bone growth complex of claim 10;

surgically enlarging the mastoid cavity; and removing any recurrence of cholesteatoma removed by milling out the mastoid prior to implanting said complex.

13. The method according to claim 11 wherein said complex is made according to the method of claim 1.

* * * * *